US009925388B2

(12) United States Patent
Andalib et al.

(10) Patent No.: US 9,925,388 B2
(45) Date of Patent: Mar. 27, 2018

(54) DEVICE AND METHOD FOR DEEP TRANSCRANIAL MAGNETIC STIMULATION

(71) Applicant: Northeastern University, Boston, MA (US)

(72) Inventors: Parisa Andalib, Malden, MA (US); Francesca Scire Scappuzzo, Lexington, MA (US); Vincent Harris, Sharon, MA (US)

(73) Assignee: Northeastern University, Boston, MA (US)

( * ) Notice: Subject to any disclaimer, the term of this patent is extended or adjusted under 35 U.S.C. 154(b) by 215 days.

(21) Appl. No.: 14/670,214

(22) Filed: Mar. 26, 2015

(65) Prior Publication Data

US 2015/0273233 A1 Oct. 1, 2015

Related U.S. Application Data

(60) Provisional application No. 61/970,860, filed on Mar. 26, 2014.

(51) Int. Cl.
*A61F 2/00* (2006.01)
*A61N 2/02* (2006.01)
*A61N 2/00* (2006.01)

(52) U.S. Cl.
CPC .............. *A61N 2/02* (2013.01); *A61N 2/006* (2013.01)

(58) Field of Classification Search
CPC .......... A61N 2/00; A61N 2/002; A61N 2/004; A61N 2/006; A61N 2/008; A61N 2/02;
(Continued)

(56) References Cited

U.S. PATENT DOCUMENTS 4,359,706 A * 11/1982 Flack .................. H01F 7/00
335/281
5,142,232 A 8/1992 Konishi et al.
(Continued)

FOREIGN PATENT DOCUMENTS

WO  2009/033144 A2  3/2009

OTHER PUBLICATIONS

L. Gomez, et al., "Numerical Analysis and Design of Single-Source Multicoil TMS for Deep and Focused Brain Stimulation", IEEE Transactions on Biomedical Engineering, Oct. 2013, vol. 60, No. 10, pp. 2771-2782.
(Continued)

*Primary Examiner* — Charles A Marmor, II
*Assistant Examiner* — Carrie R Dorna
(74) *Attorney, Agent, or Firm* — Posternak Blankstein & Lund LLP

(57) ABSTRACT

Devices and methods for directing a magnetic field into a body party of a subject are provided. The devices include at least one electromagnetic coil, a magnetic core or yoke, and a pair of flux concentrators. The flux concentrators are separated by a gap into which the body part fits and through which the flux concentrators focus the magnetic field. The devices allow magnetic fields to be transmitted through the gap with higher intensity at greater distances from the device than possible with previous designs. The methods of using such devices allow the delivery of magnetic fields with higher intensity to the interior of a body part without exposing interposed proximal regions to magnetic fields of unduly high intensity. The devices and methods are useful for deep transcranial magnetic stimulation of the brain to treat various medical conditions.

27 Claims, 10 Drawing Sheets

(58) Field of Classification Search
CPC .... A61N 2/06; H01F 3/00; H01F 3/02; H01F 3/04; H01F 3/06; H01F 3/08; H01F 3/14; H01F 7/00; H01F 7/06; H01F 7/08; H01F 7/081; H01F 7/10; H01F 27/24; H01F 27/245; H01F 27/2455; H01F 27/25; H01F 27/255; H01F 27/28; H01F 27/2895

See application file for complete search history.

(56) References Cited

U.S. PATENT DOCUMENTS

| | | | | |
|---|---|---|---|---|
| 5,315,276 | A | 5/1994 | Huson et al. | |
| 6,210,317 | B1* | 4/2001 | Bonlie | A61N 2/02 600/9 |
| 6,235,251 | B1* | 5/2001 | Davidson | A61N 2/02 422/186.01 |
| 6,572,528 | B2 | 6/2003 | Rohan et al. | |
| 7,407,478 | B2 | 8/2008 | Langen et al. | |
| 7,520,848 | B2 | 4/2009 | Schneider et al. | |
| 8,052,591 | B2 | 11/2011 | Mishelevich et al. | |
| 2002/0169355 | A1* | 11/2002 | Rohan | A61N 2/02 600/9 |
| 2004/0143300 | A1* | 7/2004 | Rogers | A61N 2/02 607/45 |
| 2007/0027353 | A1* | 2/2007 | Ghiron | A61N 2/02 600/9 |
| 2007/0260107 | A1* | 11/2007 | Mishelevich | A61N 2/004 600/14 |

OTHER PUBLICATIONS

M. Lu, et al., "Calculating the Induced Electromagnetic Fileds in real Human Head by Deep Transcranial Magnetic Stimulation", 35th Annual International Conference of the IEEE EMBS, Osaka, Japan Jul. 3-7, 2013, pp. 795-798.

G. Xu, et al., "The Optimal Design of Magnetic Coil in Transcranial Magnetic Stimulation", Proceedings of the 2005 IEEE Engineering in medicine and Biology 27th Annual Conference, Shanghai, China, Sep. 1-4, 2005, pp. 5221-6224.

R. Salvador, et al., "High-Permeability Core Coils for Transcranial Magnetic Stimulation of Deep Brain Regions", Proceedings of the 29th Annual International Conference of the IEEE EMBS Cite Internationale, Lyon, France, Aug. 23-26, 2007, pp. 6652-6655.

S. Rossi, et al., "Safety, ethical considerations, and application guidelines for the use of transcranial magnetic stimulation in clinical practice and research", Clinical Neurophysiology, (2009), vol. 120, pp. 2008-2039.

J. Ruohonen, "Transcranial Magnetic Stimulation: Modelling and New Techniques", Dissertation for Doctorate of Technology, Helsinki University of Technology, Espoo, Finland, Dec. 4, 1998, 52 pgs.

Y. Roth, et al., "A Coil Design for Transcranial Magnetic Stimulation of Deep Brain Regions", Journal of Clinical Neurophysiology, (2002), vol. 19, No. 4, pp. 361-370.

S. Gabriel, et al., "The dielectric properties of biological tissues: III. Parametric models for the dielectric spectrum of tissues", Physics in Medicine and Biology, (1996), vol. 41, Issue 11, pp. 2271-2293.

H. A. Sackheim, "Magnetic Stimulation Therapy and ECT", Convulsive Therapy, (1994), vol. 10, No. 4, pp. 255-258.

\* cited by examiner

DEVICE AND METHOD FOR DEEP TRANSCRANIAL MAGNETIC STIMULATION

CROSS REFERENCE TO RELATED APPLICATIONS

This application claims the benefit of U.S. Provisional Application No. 61/970,860 filed Mar. 26, 2014 and entitled "Deep field penetration in transcranial magnetic stimulation (TMS) via magnetic flux concentrator and strategic excitation coil placement," which is hereby incorporated by reference in its entirety.

BACKGROUND

Transcranial Magnetic Stimulation (TMS) and Repetitive Transcranial Magnetic Stimulation (rTMS, a variant of TMS in which electromagnetic fields are produced in trains of multiple short pulses) can trigger neuronal firing in selected brain regions. TMS-induced neuronal firing may be therapeutically effective for at least one psychiatric condition, major depression. Because a magnetic field always diminishes as a function its distance from the source, however, TMS and rTMS instrumentation is currently limited by the inability to focus the magnetic fields at depths without discomfort to the patient.

Attempts have been made to focus electromagnetic energy into deep structures of the brain without overwhelming superficial structures. For example, efforts have been made to simultaneously use multiple coils such that the magnetic fields converge at a chosen point (see Sackheim, H A. Magnetic Stimulation Therapy and ECT (Commentary) Convulsive Therapy, 1994, 10(4): 255-8). Even if feasible for achieving greater penetration, however, the difficulty of coordinating the fields from multiple coils (e.g., adjusting for a specific target) makes this approach sub-optimal.

U.S. Pat. No. 6,572,528, describes the use of an adaptation of a 1.5 Tesla MRI scanner to produce some form of transcranial magnetic stimulation. In this machine, the largest magnet (the solenoid) remains stationary and at steady state, while the programmable magnets (e.g., the head coil and the gradient coil) are of relatively low field strength. Consequently, such a configuration may not be able to selectively stimulate targeted deep brain structures while sparing superficial structures.

A variety of new electromagnet configurations have been developed by the Helsinki group (Ruohonen, J, Dissertation for Doctorate of Technology, Helsinki University of Technology, Espoo, Finland, 1998), which may be useful in the context of TMS for reaching to deeper structures. However, these magnets pass the majority of their energy through interposed proximal tissue and thus can have undesired side off-target effects when used for deep TMS.

Specially-shaped coils that provide more gradual decrease in magnetic field as a function of distance from the coil have been reported (see, e.g., Roth, Y; Zangen, A; Hallet, M; Journal of Clinical Neurophysiology, 2002, 19(4): 361-370). In addition, multiple-coil configurations have been tested for the ability to stimulate deep brain structures (see George, M S Stimulating the Brain, Scientific American, editor's inset window, page 72 September 2003). Such devices, however, are likely to be inflexible and may require different coil arrays to target different brain regions or even to target the same brain region in two different individuals.

Another mechanism of targeting magnetic fields to specific structures is to attach mechanical or computerized stereotactic neurosurgical image guidance systems to TMS coils (e.g., STEALTH STATION by Surgical Navigation Technologies, Inc., Broomfield Colo.). These methods also suffer from the problem of providing strong and potentially harmful magnetic fields to intervening tissue in an effort to provide ample stimulation to the targeted structures.

Consequently, there remains a need for devices and methods by which magnetic fields can be directed so as to selectively affect deep-targeted structures while leaving superficial structures relatively undisturbed.

SUMMARY OF THE INVENTION

One aspect of the invention is a device capable of directing a magnetic field into a body part of a subject, the device including: a ferromagnetic yoke having two ends, the two ends disposed at opposite ends of the yoke, the yoke including flux concentrators at each end of the yoke and connecting element that connects the flux concentrators; and at least one coil surrounding the connecting element of the yoke, the coil capable of carrying an electric current that generates a magnetic field along the yoke, wherein the flux concentrators are separated by a gap sufficient to accommodate the body part.

In some embodiments, each end of the yoke is circular in a plane orthogonal to a longitudinal dimension extending from the end of the yoke. In some embodiments, each end of the yoke is ellipsoidal in a plane orthogonal to a longitudinal dimension extending from the end of the yoke.

In some embodiments, the flux concentrators include concave spherical caps. In some embodiments, the concave spherical caps of the flux concentrators have radii of curvature of from about 1 cm to about 200 cm, from about 1 cm to about 300 cm, from about 1 cm to about 400 cm, from about 1 cm to about 500 cm, from 1 cm to infinity, from about 1 cm to about 100 cm, from about 2 cm to about 80 cm, from about 3 cm to about 60 cm, from about 4 cm to about 40 cm, from about 5 cm to about 30 cm, from about 6 cm to about 20 cm, from about 7 cm to about 15 cm, from about 8 cm to about 10 cm, from about 2 cm to about 30 cm, from about 3 cm to about 25 cm, from about 4 cm to about 20 cm, from about 5 cm to about 15 cm, or from about 6 cm to about 12 cm, about 1 cm, about 2 cm, about 5 cm, about 10 cm, about 15 cm, about 20 cm, about 40 cm, about 50 cm, about 60 cm, about 70 cm, about 80 cm, about 90 cm, about 100 cm, about 120 cm, about 150 cm, about 200 cm, about 300 cm, about 400 cm, about 500 cm, or greater than 500 cm. In some embodiments the flux concentrators include a disc. In some embodiments the flux concentrators include a parabaloid or a portion thereof or an ellipsoid are a portion thereof.

In some embodiments the two flux concentrators are identical or nearly identical in shape and size. In some embodiments, the two flux concentrators differ in shape, in size, or in both shape and size.

In some embodiments, the longitudinal dimensions extending from the ends of the yoke intersect to form an angle of from about 90° to about 270°, from about 100° to about 260°, from about 110° to about 250°, from about 120° to about 240°, from about 130° to about 230°, from about 140° to about 220°, from about 150° to about 210°, from about 160° to about 200°, from about 170° to about 190°, or about 180°.

In some embodiments, the region of the yoke including the flux concentrator is cylindrical. In some embodiments, the region of the yoke including the flux concentrator is flared. In some embodiments, the region of the yoke including the flux concentrator is tapered.

In some embodiments the device is capable of providing a magnetic field strength of from about 0.5 T to about 4 T, from about 1 T to about 3 T, from about 1.5 T to about 2.5 T, at least 0.5 T, at least 1 T, at least 1.5 T, at least 2 T, at least 2.5 T, or at least 3 T within the body part at a distance of 4 cm from each of the flux concentrators. In some embodiments, the device is capable of providing a magnetic field that has an intensity not greater than 4 T, 3.9 T, 3.8 T, 3.7 T, 3.6 T, 3.5 T, 3.4 T, 3.3 T, 3.2 T, 3.1 T, 3 T, 2.9 T, 2.8 T, 2.7 T, 2.6 T, 2.5 T, 2.4 T, 2.3 T, 2.2 T, 2.1 T, 2 T, 1.9 T, 1.8 T, 1.7 T, 1.6 T, 1.5 T, 1.4 T, 1.3 T, 1.2 T, 1.1 T, or 1 T at the ends of the yokes but an intensity at least 0.5 T, 0.6 T, 0.7 T, 0.8 T, 0.9 T, 1 T, 1.1 T, 1.2 T, 1.3 T, 1.4 T, 1.5 T, 1.6 T, 1.7 T, 1.8 T, 1.9 T, 2 T, 2.1 T, 2.2 T, 2.3 T, 2.4 T, 2.5 T, 2.6 T, 2.7 T, 2.8 T, 2.9 T, 3 T, 3.1 T, 3.2 T, 3.3 T, 3.4 T, 3.5 T, 3.6 T, 3.7 T, 3.8 T, 3.9 T, or 4 T at a point 4 cm from each the end of the yoke along a longitudinal dimension extending from each end of the yoke.

In some embodiments, the ferromagnetic yoke has a coercivity of less than 500 Oe. In some embodiments, the ferromagnetic yoke contains silicon steel, a metallic glass, or a ferrite. In some embodiments, the yoke has a longitudinal length of from about 10 cm to about 10 m. In some embodiments the ends of the yoke have maximal diameters from about 1 cm to about 100 cm, from about 2 cm to about 80 cm, from about 3 cm to about 60 cm, from about 4 cm to about 40 cm, from about 5 cm to about 30 cm, from about 6 cm to about 20 cm, from about 7 cm to about 15 cm, from about 8 cm to about 10 cm, from about 2 cm to about 30 cm, from about 3 cm to about 25 cm, from about 4 cm to about 20 cm, from about 5 cm to about 15 cm, or from about 6 cm to about 12 cm.

In some embodiments, the device has a single coil surrounding the connecting element of the yoke at a point equidistant from each end of the yoke along the longitudinal length of the connecting element. In some embodiments, the device has two coils of opposite polarity surrounding the connecting element. In some embodiments, the device has one coil surrounding the connecting element of the yoke at a distance from one end of the yoke along the longitudinal length of the connecting element and another coil surrounding the connecting element of the yoke at about the same distance the other end of the yoke along the longitudinal length of the connecting element. In some embodiments, the distances along the longitudinal length of the yoke between the coils and the ends of the yoke is from about 5 cm to about 100 cm. In some embodiments, the device has three or more coils surrounding the connecting element and placed at symmetrical positions with respect to the two ends of the yoke.

In some embodiments, the connecting element of the ferromagnetic yoke is rigid. In some embodiments, the connecting element of the ferromagnetic yoke is flexible. In some embodiments, the connecting element of the yoke is C-shaped. In some embodiments, the connecting element of the yoke has semispherical arcs proximal to each end and a straight central portion between the semispherical arcs. In some embodiments, the connecting element is substantially planar. In some embodiments, the shape of the connecting element is three-dimensional (non-planar).

In some embodiments, the distance across the gap between the centers of the ends of the yoke is from about 5 cm to about 50 cm, from about 10 cm to about 40 cm, from about 10 cm to about 30 cm, from about 15 cm to about 30 cm, or from about 20 cm to about 25 cm. In some embodiments, the center points of the spherical caps of the flux concentrators are separated by a distance across the gap of from about 5 cm to about 50 cm, from about 10 cm to about 40 cm, from about 10 cm to about 30 cm, from about 15 cm to about 30 cm, or from about 20 cm to about 25 cm.

In some embodiments, the body part is a head, neck, skull, brain, chest, abdomen, limb, arm, hand, leg, or foot.

In some embodiments, the device includes a coil capable of modifying the magnetic field within the body part.

In another aspect, the invention includes a system including: a device of the invention, a controller, and a power supply capable of providing an alternating current to the coil or coils, thereby generating a magnetic field between the flux concentrators.

In some embodiments, the system includes a coil capable of modifying the magnetic field within the body part.

In another aspect, the invention includes a method of directing a magnetic field into a body part of a subject, the method including applying an alternating current to at least one coil positioned at least 1 cm, at least 2 cm, at least 3 cm, at least 4 cm, at least 5 cm, at least 6 cm, at least 7 cm, at least 8 cm, at least 9 cm, or at least 10 cm from the surface of the body part and directing a magnetic field having an intensity of at least 0.5 T, 0.6 T, 0.7 T, 0.8 T, 0.9 T, 1 T, 1.1 T, 1.2 T, 1.3 T, 1.4 T, 1.5 T, 1.6 T, 1.7 T, 1.8 T, 1.9 T, 2 T, 2.1 T, 2.2 T, 2.3 T, 2.4 T, 2.5 T, 2.6 T, 2.7 T, 2.8 T, 2.9 T, 3 T, 3.1 T, 3.2 T, 3.3 T, 3.4 T, 3.5 T, 3.6 T, 3.7 T, 3.8 T, 3.9 T, or 4 T at an interior region located at least 4 cm from the surface of said body part.

In another aspect, the invention includes a method of directing a magnetic field into a body part of a subject, the method including the steps of: positioning a device of the invention so that the body part is within the gap, the part having a first surface adjacent to a first end of the yoke and a second surface adjacent to the second end of the yoke; and applying an alternating electric current to the coil or coils, whereby a magnetic field is generated in an interior region of the body part.

In some embodiments, the distance from one flux concentrator to a surface of the body part and the distance from the other flux concentrator to another surface of the body part are about the same or different. In some embodiments, the distance from one flux concentrator to a surface of the body part and the distance from the other flux concentrator to another surface of the body part are about the same. In some embodiments, the distance from one flux concentrator to a surface of the body part and the distance from the other flux concentrator to another surface of the body part are different. In some embodiments, the distance from one flux concentrator to a surface of the body part and the distance from the other flux concentrator to another surface of the body part are less than 100 mm, less than 90 mm, less than 80 mm, less than 70 mm, less than 60 mm, less than 50 mm, less than 40 mm, 30 mm, less than 25 mm, less than 20 mm, less than 15 mm, less than 10 mm, less than 5 mm, from about 5 mm to about 30 mm, from about 5 mm to about 25 mm, from about 5 mm to about 20 mm, from about 5 mm to about 15 mm, or from about 5 mm to about 10 mm.

In some embodiments, the interior region of the body part is at least 1 cm, at least 2 cm, at least 3 cm, at least 4 cm, at least 5 cm, at least 6 cm, at least 7 cm, at least 8 cm, at least 9 cm, or at least 10 cm from the surfaces of the body part that are proximal to the flux concentrators. In some embodiments, the interior region of the body part is at least 1 cm, at least 2 cm, at least 3 cm, at least 4 cm, at least 5 cm, at least 6 cm, at least 7 cm, at least 8 cm, at least 9 cm, or at least 10 cm from the surface of the body part that is proximal to one flux concentrator.

In some embodiments, magnetic field strength is from about 0.5 T to about 5 T, from about 1 T to about 4 T, from about 1 T to about 3 T, from about 1.5 T to about 2.5 T, at least 0.5 T, at least 1 T, at least 1.5 T, at least 2 T, at least 2.5 T, or at least 3 T within the body part at a distance of 4 cm from each of the flux concentrators. In some embodiments, magnetic field strength is from about 0.5 T to about 4 T, from about 1 T to about 3 T, from about 1.5 T to about 2.5 T, at least 0.5 T, at least 1 T, at least 1.5 T, at least 2 T, at least 2.5 T, or at least 3 T at a distance of 4 cm from the surfaces of the body part that are proximal to the flux concentrators. In some embodiments, magnetic field strength is from about 0.5 T to about 4 T, from about 1 T to about 3 T, from about 1.5 T to about 2.5 T, at least 0.5 T, at least 1 T, at least 1.5 T, at least 2 T, at least 2.5 T, or at least 3 T at a distance of 4 cm from the surface of the body part that is proximal to one flux concentrator. In some embodiments, the magnetic field has an intensity not greater than 4 T, 3.9 T, 3.8 T, 3.7 T, 3.6 T, 3.5 T, 3.4 T, 3.3 T, 3.2 T, 3.1 T, 3 T, 2.9 T, 2.8 T, 2.7 T, 2.6 T, 2.5 T, 2.4 T, 2.3 T, 2.2 T, 2.1 T, 2 T, 1.9 T, 1.8 T, 1.7 T, 1.6 T, 1.5 T, 1.4 T, 1.3 T, 1.2 T, 1.1 T, or 1 T at the surfaces of the body part but an intensity at least 0.5 T, 0.6 T, 0.7 T, 0.8 T, 0.9 T, 1 T, 1.1 T, 1.2 T, 1.3 T, 1.4 T, 1.5 T, 1.6 T, 1.7 T, 1.8 T, 1.9 T, 2 T, 2.1 T, 2.2 T, 2.3 T, 2.4 T, 2.5 T, 2.6 T, 2.7 T, 2.8 T, 2.9 T, 3 T, 3.1 T, 3.2 T, 3.3 T, 3.4 T, 3.5 T, 3.6 T, 3.7 T, 3.8 T, 3.9 T, or 4 T at points 4 cm from the surfaces of the body part along longitudinal dimensions extending from each end of the yoke.

In some embodiments, the current has an amplitude of from about 1 kA to about 30 kA, from about 2 kA to about 25 kA, from about 5 kA to about 20 kA, from about 6 kA to about 15 kA, from about 8 kA to about 12 kA, or about 10 kA. In some embodiments, the alternating current has a frequency of from about 1 kHz to about 20 kHz, from about 2 kHz to about 15 kHz, from about 3 kHz to about 12 kHz, from about 3.5 kHz to about 10 kHz, from about 4 kHz to about 8 kHz, from about 4 kHz to about 6 kHz, or about 5 kHz.

In some embodiments, the current is applied in a single pulse of about 0.01 ms, about 0.02 ms, about 0.05 ms, about 0.1 ms, about 0.2 ms, about 0.5 ms, about 1 ms, about 2 ms, about 5 ms, about 10 ms, about 20 ms, or about 50 ms. In some embodiments, the current is applied in a plurality of pulses of about 0.01 ms, about 0.02 ms, about 0.05 ms, about 0.1 ms, about 0.2 ms, about 0.5 ms, about 1 ms, about 2 ms, about 5 ms, about 10 ms, about 20 ms, or about 50 ms.

In some embodiments, the interior region of the body part is the anterior cingulate gyms, anterior cingulate, anterior limb of the internal capsule, dorsal cingulate gyms, globus pallidus extema, hippocampus, nucleus accumbens, posterior cingulate gyms, septal nucleus, subgenual cingulate gyms, subthalamic nucleus, ventrolateral nucleus of thalamus, or ventromedial nucleus of thalamus.

In some embodiments, the method is for the treatment of a disease or condition. In some embodiments the disease or condition is a disease or condition of the brain. In some embodiments, the disease or condition is addiction, Alzheimer's disease, anxiety disorder, chronic pain, depression, essential tremor, hippocampal sclerosis, memory disorders, mesial temporal sclerosis (MTS), neurodegenerative conditions, obesity, obsessive compulsive disorders, Parkinson's disease, seizure, substance abuse, stroke, temporal lobe epilepsy (TLE), tinnitus, or tremors.

In another aspect, the invention includes a method of directing a magnetic field into a body part of a subject, the method including the steps of: rotating a device of the invention around the body part; and applying current to the coil from a plurality of locations to direct magnetic fields to an interior region of the body part, wherein the current is applied to the coil at a sufficiently rapid frequency to prevent re-polarization of the interior region as the device is rotated, such that the magnetic stimulation of the interior region is higher than at other regions interposed between the interior region and the flux concentrators.

DETAILED DESCRIPTION OF THE INVENTION

The present invention relates to devices and methods for electromagnetic stimulation of target areas, typically within the anatomy of a living organism such as a human medical patient or an animal. Devices of the invention employ a ferromagnetic core, or yoke, to direct the magnetic field generated by an electric coil into media beyond the end of the yoke. The devices of the invention allow magnetic fields to be transmitted over greater distances through air and other media with higher field strengths. Consequently, the devices and methods of the invention can be used to provide a stronger magnetic field to an interior portion of a subject, e.g., an internal region of the brain, without causing unintended off-target effects to more superficial regions that lie within the path of the magnetic field.

Figure 1:
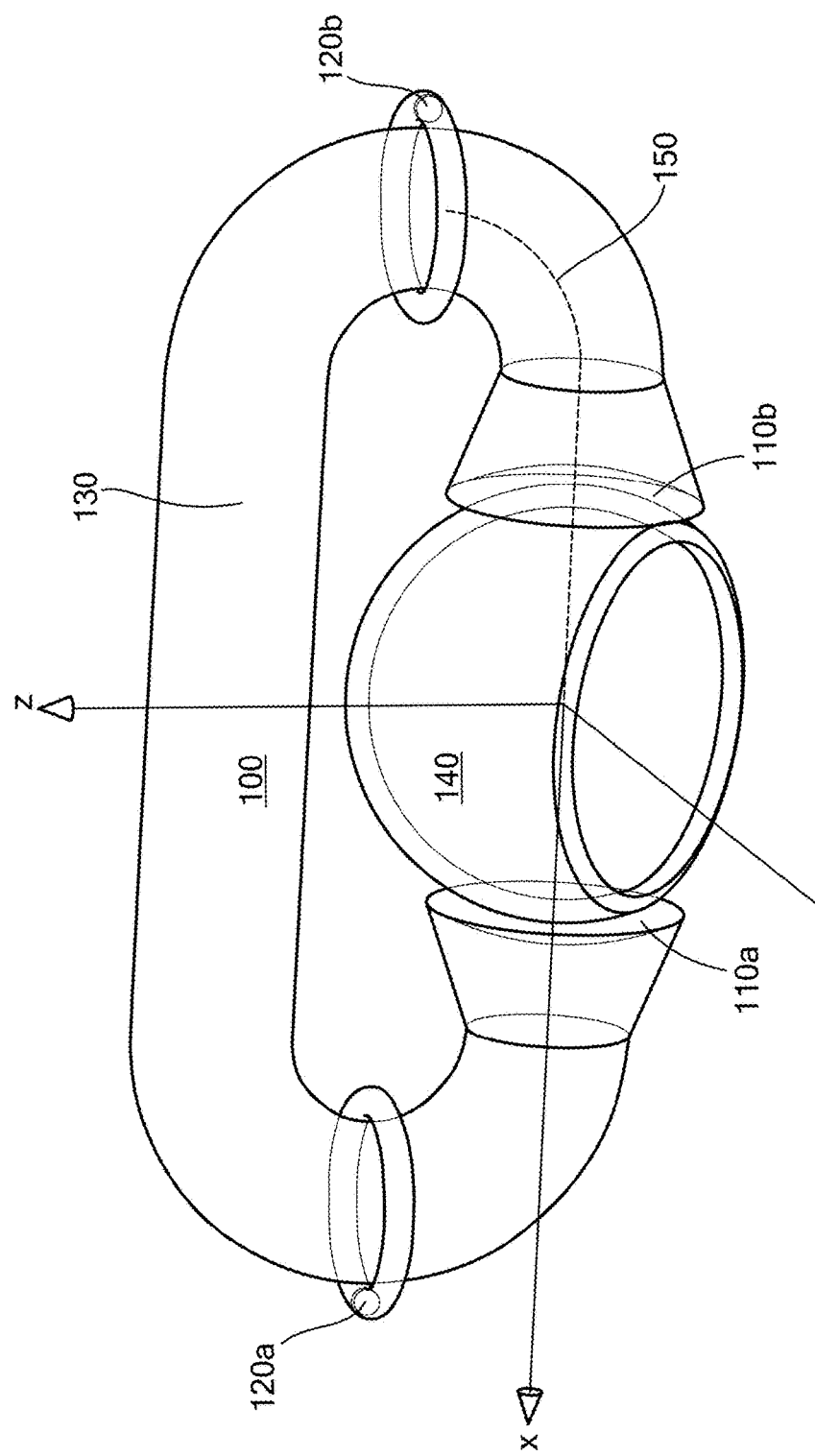
FIG. 1 is a schematic of a magnetic field device of the invention with the flux concentrators on opposite sides of a spherical shell. The spherical shell serves as a model for the head of a subject, to which a magnetic field would be applied during operation of the device.

An embodiment of a device of the invention is shown in FIG. 1. The device includes a ferromagnetic yoke (100) that has two opposite ends. The yoke includes a pair of flux concentrators (110a and 110b), one positioned at each end of the yoke. The yoke also includes a connecting element (130) that connects the two flux concentrators. The surfaces of the flux concentrators distal to the connecting element face each other and are separated by a gap large enough to accommodate a body part. The device of FIG. 1 has a model of a head (140) situated in the gap between the flux concentrators. Surrounding a portion of the connecting element of the yoke is one or more coils (120a and 120b). The embodiment shown in FIG. 1 has two coils, but other embodiments may have one coil, three coils, or more. Each coil is positioned at a distance along the longitudinal length of the connecting element from each end of the yoke; one such distance (150) is shown in FIG. 1. In embodiments in which one coil is used, the distances along the longitudinal length of the connecting element from the two ends of the yoke may be about the same. In embodiments in which two coils are used, a first coil is positioned closer to the first end of the yoke, and a second coil is positioned closer to the other end of the yoke. In such embodiments, the distances along the longitudinal length of the connecting element from the first coil to the first end of the yoke and from the second coil to the second end of the yoke may be about the same, i.e., the coils may be positioned symmetrically along the yoke. These distances may be from about 5 cm to about 100 cm. If three or more coils are used, they may also be positioned symmetrically along the yoke.

As used herein, a "terminus" of the yoke is a portion of the yoke that includes a flux concentrator. The terminus may be cylindrical. Alternatively, the terminus may take the shape of a conical frustum with a greater diameter at the end of the yoke (a "flared" terminus), with a small diameter at the end of the yoke (a "tapered" terminus), or it may have both flared and tapered regions.

Figure 2A:
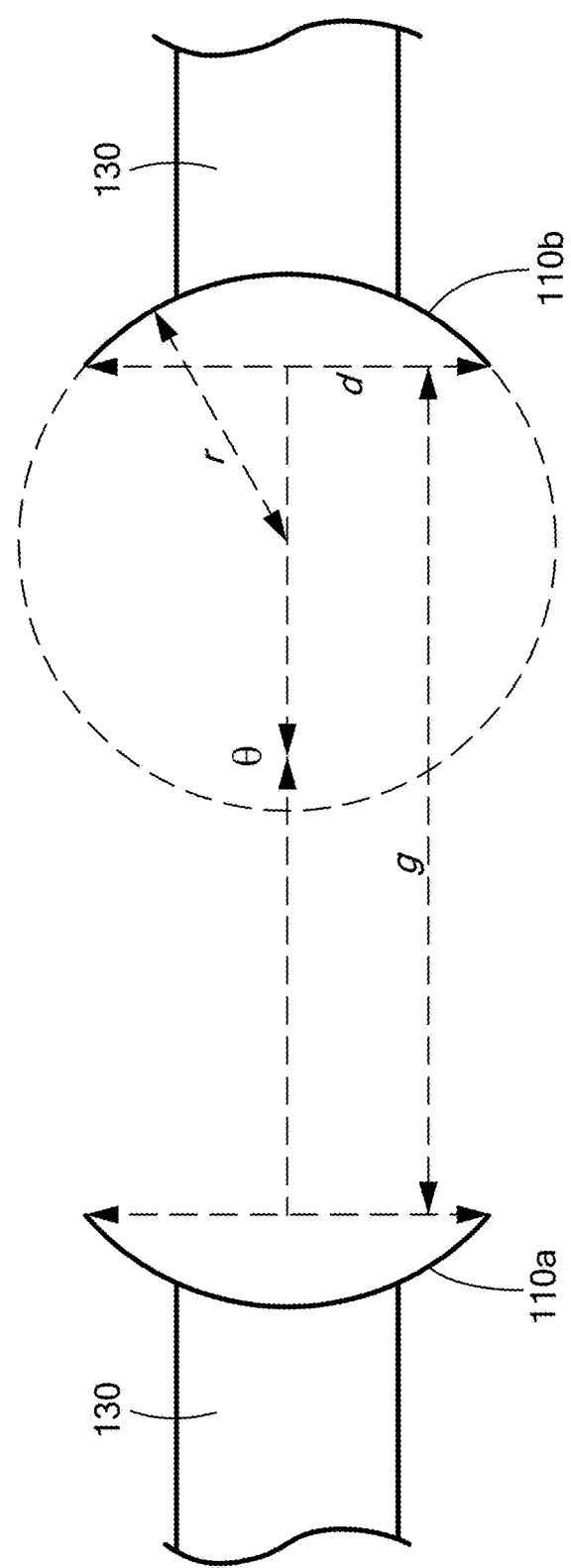
FIG. 2A is a schematic of two concave, spherical-cap flux concentrators of a magnetic field-generating device in an embodiment of the invention. d represents the diameter of the curved surface of the spherical cap, r represents the radius of curvature of the spherical cap, g represents the distance across the gap between the planes comprising the edges of the curved surfaces of the two flux concentrators, and θ represents the angle formed by the intersection of the longitudinal dimensions extending from each end of the yoke.

The flux concentrators may have any shape that allows them to concentrate the magnetic field emitted from the ends of the yoke. They may be concave spherical caps, as shown in FIG. 1. As shown in FIG. 2A, concave spherical caps of the flux concentrators have a radius of curvature r. The radius of curvature may be from about 1 cm to about 200 cm, from about 1 cm to about 300 cm, from about 1 cm to about 400 cm, from about 1 cm to about 500 cm, from about 1 cm to about 100 cm, from about 2 cm to about 80 cm, from about 3 cm to about 60 cm, from about 4 cm to about 40 cm, from about 5 cm to about 30 cm, from about 6 cm to about 20 cm, from about 7 cm to about 15 cm, from about 8 cm to about 10 cm, from about 2 cm to about 30 cm, from about 3 cm to about 25 cm, from about 4 cm to about 20 cm, from about 5 cm to about 15 cm, or from about 6 cm to about 12 cm, about 1 cm, about 2 cm, about 5 cm, about 10 cm, about 15 cm, about 20 cm, about 40 cm, about 50 cm, about 60 cm, about 70 cm, about 80 cm, about 90 cm, about 100 cm, about 120 cm, about 150 cm, about 200 cm, about 300 cm, about 400 cm, or about 500 cm. Alternatively, the flux concentrators may be discs or any other shape suitable for the purpose. The two flux concentrators may be identical or nearly identical in shape and size, or they may differ in shape, size, or both. As shown in FIG. 2A, the size of the of flux concentrator can be described by a diameter d, which represents the longest distance across the widest dimension of the flux concentrator. For a flux concentrator shaped as a spherical cap, as shown in FIG. 2A, the diameter d is the diameter across the edge of the curved surface. For a flux concentrator shaped as a disc, the diameter d is the diameter of the disc. The diameter of the flux concentrator may be from about 1 cm to about 100 cm, from about 2 cm to about 80 cm, from about 3 cm to about 60 cm, from about 4 cm to about 40 cm, from about 5 cm to about 30 cm, from about 6 cm to about 20 cm, from about 7 cm to about 15 cm, from about 8 cm to about 10 cm, from about 2 cm to about 30 cm, from about 3 cm to about 25 cm, from about 4 cm to about 20 cm, from about 5 cm to about 15 cm, or from about 6 cm to about 12 cm. In embodiments in which the ends of the yoke comprise flux concentrators, the diameter d of a flux concentrator can be considered equivalent to the diameter across the end of the yoke.

Figure 2B:
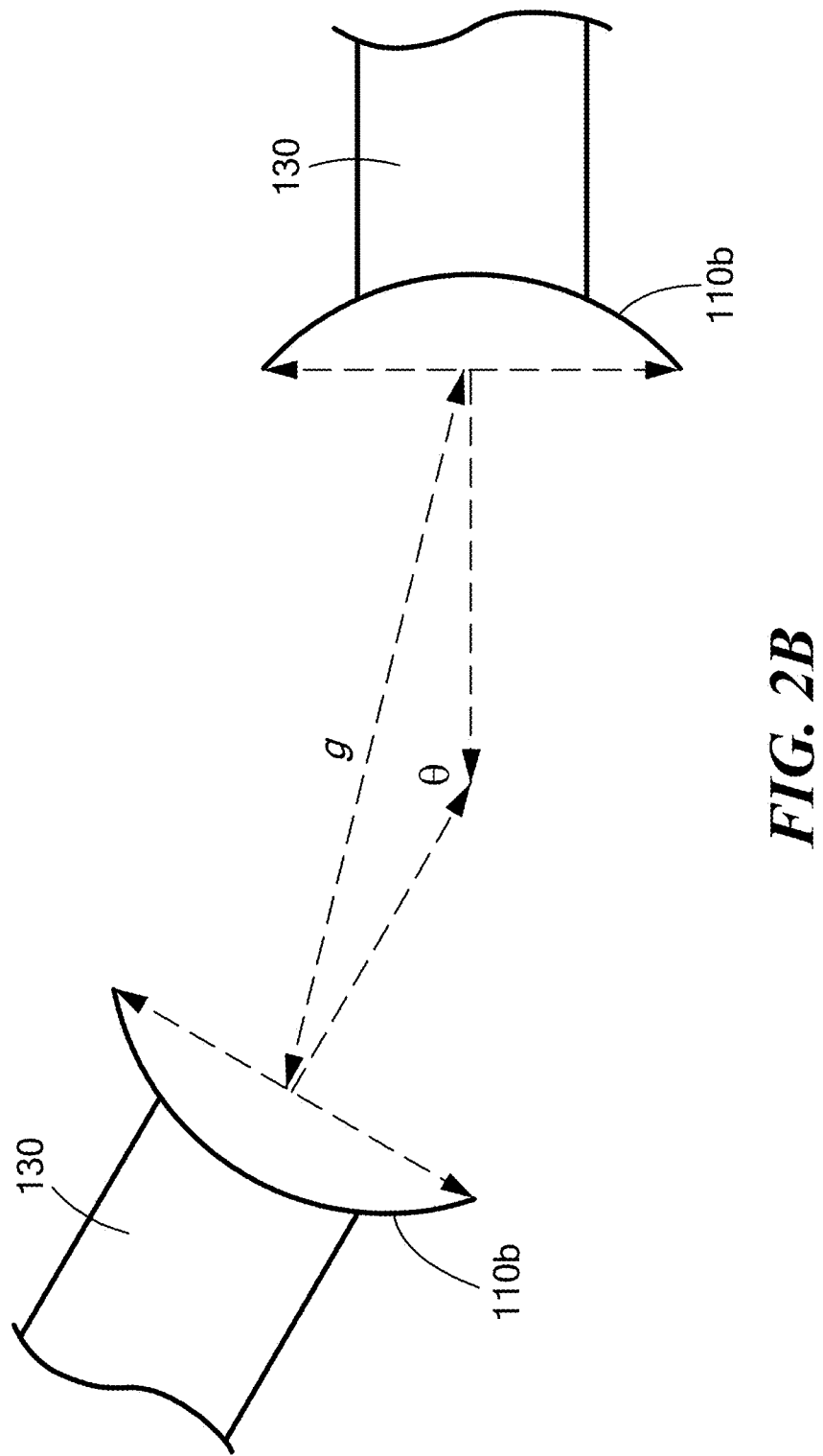
FIG. 2B is a schematic of two concave, spherical-cap flux concentrators of a magnetic field-generating device in another embodiment of the invention.
Figure 2C:
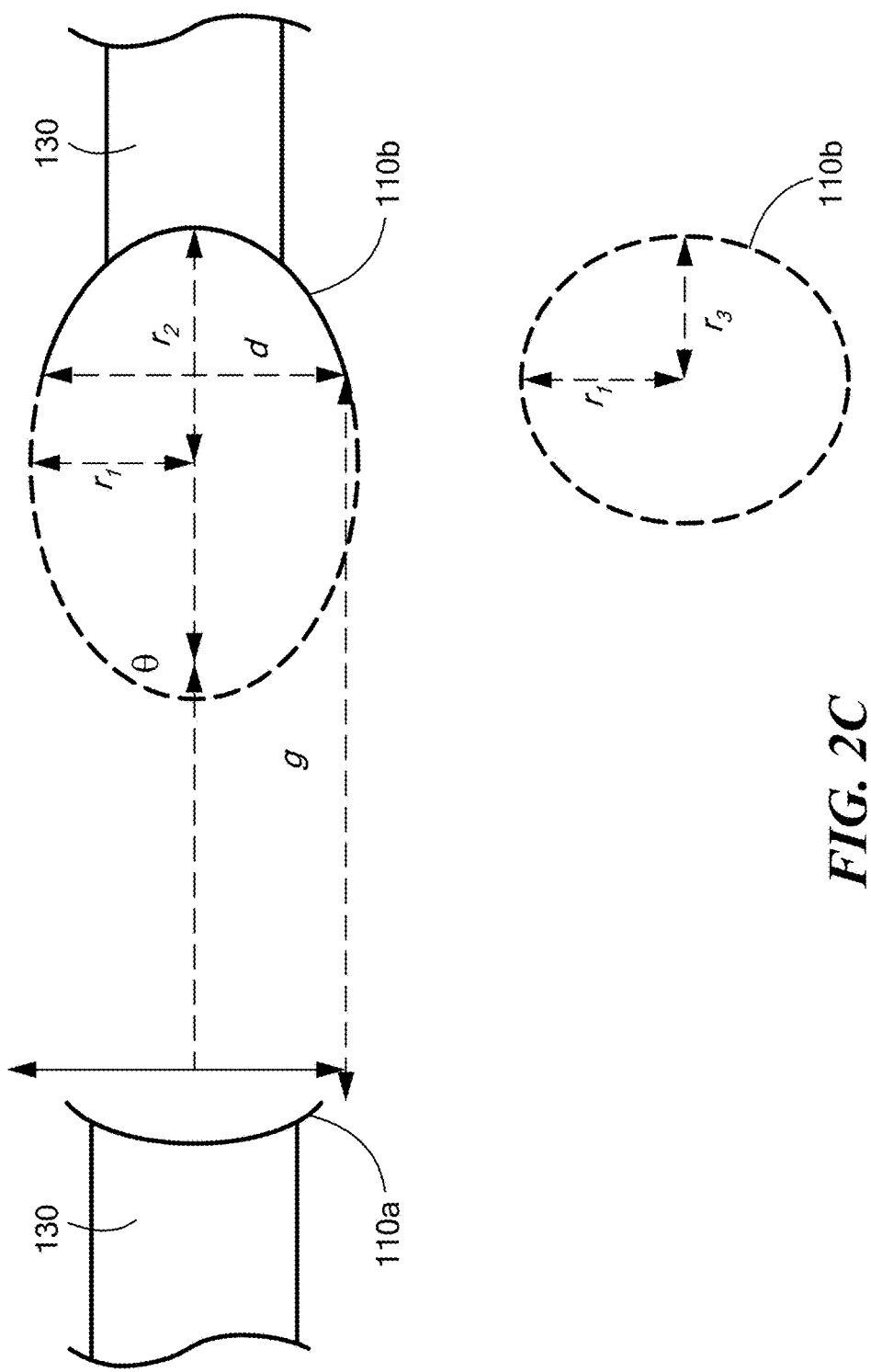
FIG. 2C is a schematic of two concave, ellipsoidal flux concentrators of a magnetic field-generating device in an embodiment of the invention. Bottom is a cross-sectional view of the flux concentrator on the right. d represents the diameter of the curved surface of the ellipsoidal cap, $r_1$, $r_2$ and $r_3$ represent the three radii of curvature of the ellipsoid cap, g represents the distance across the gap between the planes comprising the edges of the curved surfaces, and θ represents the angle formed by the intersection of the longitudinal dimensions extending from each end of the yoke.

The flux concentrators are considered to be facing each other as long as they are positioned in a way that allows a magnetic field to flow across the gap between them. They need not be diametrically opposed. Because the flux concentrators are disposed at the ends of the yoke, the spatial relationship of the flux concentrators can be defined an angle $\theta$ at which the longitudinal dimensions extending from the two ends of the yoke meet, as shown in FIG. 2A. In a preferred embodiment, $\theta=180°$. An alternate embodiment having $\theta=150°$ is shown in FIG. 2B. The angle of intersection, $\theta$, between the longitudinal dimension of the two ends of the yoke may be from about 90° to about 270°, from about 100° to about 260°, from about 110° to about 250°, from about 120° to about 240°, from about 130° to about 230°, from about 140° to about 220°, from about 150° to about 210°, from about 160° to about 200°, from about 170° to about 190°, or about 180°.

For the purpose of measuring distances to the end of the yoke, the "end" or "end of the yoke" is considered to be the most distal plane orthogonal to the longitudinal dimension of the terminus of the yoke that contacts a portion of the yoke. If a flux concentrator contains a disc orthogonal to the longitudinal dimension of the terminus, the end of the yoke is the plane in which the disc lies. If a flux concentrator contains a spherical cap orthogonal to the longitudinal dimension of the terminus, the end of the yoke is the plane in which the edge of the spherical cap lies. If a flux concentrator contains a disc that is not orthogonal to the longitudinal dimension of the terminus, the end of the yoke is the plane that includes the point on the disc most distal to the remainder of the yoke, e.g., the connecting element.

The flux concentrators may be detachable from the connecting element of the ferromagnetic yoke. This enables the device to be fitted with different sets of flux concentrators for different purposes. Different applications of the device may require flux concentrators of different shapes and/or sizes. Therefore, it may be desirable to have multiple pairs of flux concentrators for use with a given device. The use of detachable flux concentrators allows a single device to function in a wide variety of applications by deploying a pair of flux concentrators optimized for each application.

An advantage of devices of the invention is that they are capable of directing magnetic fields that maintain their intensities in air, a body part, or other media better than magnetic fields provided by conventional electromagnetic coils. Thus, they can provide magnetic fields of high intensity at greater distances. The distance may be measured from a reference point, such as the center of the flux concentrator, from the end of the yoke, or from the surface of a body part positioned in the gap between the flux concentrators. The distance may be about 1 cm, about 2 cm, about 3 cm, about 4 cm, about 5 cm, about 6 cm, about 7 cm, about 8 cm, about 9 cm, or about 10 cm from the reference point. For example, the device may be capable of providing a magnetic field strength of from about 0.5 T to about 4 T, from about 1 T to about 3 T, from about 1.5 T to about 2.5 T, at least 0.5 T, at least 1 T, at least 1.5 T, at least 2 T, at least 2.5 T, or at least 3 T at a specific distance from the reference point. Alternatively, the magnetic field may be described as having an intensity below a first threshold at a reference point but above a second threshold at a distance from the reference point. For example, the magnetic field may have an intensity not greater than 4 T, 3.9 T, 3.8 T, 3.7 T, 3.6 T, 3.5 T, 3.4 T, 3.3 T, 3.2 T, 3.1 T, 3 T, 2.9 T, 2.8 T, 2.7 T, 2.6 T, 2.5 T, 2.4 T, 2.3 T, 2.2 T, 2.1 T, 2 T, 1.9 T, 1.8 T, 1.7 T, 1.6 T, 1.5 T, 1.4 T, 1.3 T, 1.2 T, 1.1 T, or 1 T at the reference point but an intensity at least 0.5 T, 0.6 T, 0.7 T, 0.8 T, 0.9 T, 1 T, 1.1 T, 1.2 T, 1.3 T, 1.4 T, 1.5 T, 1.6 T, 1.7 T, 1.8 T, 1.9 T, or 2 T at a point 4 cm from the reference point.

The gap between the flux concentrators must be wide enough to accommodate a body part positioned between them but narrow enough to maintain a continuous magnetic field of sufficient intensity to deliver an appropriate magnetic field to the intended target. The distance across the gap is measured between two reference points. As shown in FIGS. 2A and 2B, the distance across the gap, g, may be measured from the centers of the ends of the yoke. Alternatively, the distance across the gap may be measure from the centers of the flux concentrators. The distance across the gap may be, for example, from about 5 cm to about 50 cm, from about 10 cm to about 40 cm, from about 10 cm to about 30 cm, from about 15 cm to about 30 cm, or from about 20 cm to about 25 cm.

The ferromagnetic yoke may have a coercivity of less than about 20,000 Oe, about 10,000 Oe, about 7500 Oe, about 5000 Oe, about 2000 Oe, about 1000 Oe, or about 500 Oe. The ferromagnetic yoke may contain a soft ferromagnetic material. For example, the ferromagnetic yoke may contain a silicon steel (e.g., permalloy or permendur), a metallic glass (i.e., an amorphous, non-crystalline metal, such as an alloy containing boron, silicon, phosphorus, zirconium, palladium, iron, cobalt, nickel, titanium, copper, or magnesium), a ferrite (e.g., manganese zinc ferrite, nickel zinc ferrite), or carbonyl iron. The ferromagnetic yoke may contain iron, nickel, or cobalt. The yoke may have a longitudinal length of from about from about 10 cm to about 10 m. The yoke may solid or hollow. The yoke may be tubular, cylindrical, or otherwise have a circular cross-section. Alternatively, the cross-section of the yoke may be non-circular.

The connecting element of the ferromagnetic yoke may be rigid or flexible. The connecting element may be of any size and shape that allows a body part to be positioned between the flux concentrators. For example, the connecting element may be C-shaped or U-shaped. The connecting element may have curved regions and straight regions. The connecting element may assume a shape that is planar or three-dimensional.

The body part may be any body part that can have an abnormality in an interior region that can be detected, prevented, or treated by a magnetic field. For example, the body part may be a head, neck, skull, brain, chest, abdomen, limb, arm, hand, leg, or foot. The interior region may be a portion of the brain. For example, the interior region may be the anterior cingulate gyms, anterior cingulate, anterior limb of the internal capsule, dorsal cingulate gyms, globus pallidus extema, hippocampus, nucleus accumbens, posterior cingulate gyms, septal nucleus, subgenual cingulate gyms, subthalamic nucleus, ventrolateral nucleus of thalamus, or ventromedial nucleus of thalamus.

The invention also encompasses a system in which the magnetic field-generating is a component. The system may include a power supply capable of providing alternating current to the coil or coils. The system may also include a controller, processor, or housing for the device.

The magnetic field-generating device or the system containing the same may include another electromagnetic coil that does not surround the ferromagnetic yoke. The additional coil may be capable of modifying the magnetic field in the gap between the flux concentrators. The additional coil may be capable of modifying the magnetic field within a body part positioned in the gap between the ferromagnetic coils. For example, the additional coil may focus, divert, intensify, or diminish the magnetic field, or a portion thereof, in the gap between the flux concentrators. The additional coil need not be in physical contact with the yoke.

The invention also encompasses a method of directing a magnetic field into a body part of a subject by applying an alternating current to at least one coil positioned at a minimum distance from a surface of said body part and directing a magnetic field having an minimum intensity at an interior region at a specified distance from the surface of the body part. The one or more coils may be positioned at least 1 cm, at least 2 cm, at least 3 cm, at least 4 cm, at least 5 cm, at least 6 cm, at least 7 cm, at least 8 cm, at least 9 cm, or at least 10 cm from the surface of the body part. The magnetic field may have an intensity of at least 0.5 T, 0.6 T, 0.7 T, 0.8 T, 0.9 T, 1 T, 1.1 T, 1.2 T, 1.3 T, 1.4 T, 1.5 T, 1.6 T, 1.7 T, 1.8 T, 1.9 T, or 2 T at a distance of about 1 cm, about 2 cm, about 3 cm, about 4 cm, about 5 cm, about 6 cm, about 7 cm, about 8 cm, about 9 cm, or about 10 cm from the surface of the body part.

The invention also encompasses a method of directing a magnetic field into a body part of a subject using a device of the invention. In this method, a body part, such as the model of a head shown in FIG. 1, is positioned within the gap so that one surface of the body part is adjacent to one flux concentrator at one end of the yoke and another surface of the body part is adjacent to the other flux concentrator at the other end of the yoke. The distance from a reference point, such as an end of the yoke or a flux concentrator, to a surface of the body part and the distance from another reference point, such as the other end of the yoke or the other flux concentrator, to another surface of the body part may be the same or different. The distance between a reference point and the adjacent surface of the body part may be less than 30 mm, less than 25 mm, less than 20 mm, less than 15 mm, less than 10 mm, less than 5 mm, from about 5 mm to about 30 mm, from about 5 mm to about 25 mm, from about 5 mm to about 20 mm, from about 5 mm to about 15 mm, or from about 5 mm to about 10 mm.

Next, an alternating current is applied to the coil or coils to produce a magnetic field along the ferromagnetic yoke and into the body part positioned between the two flux concentrators. The current may have an amplitude of from about 1 kA to about 30 kA, from about 2 kA to about 25 kA, from about 5 kA to about 20 kA, from about 6 kA to about 15 kA, from about 8 kA to about 12 kA, or about 10 kA. The alternating current has a frequency of from about 1 kHz to about 20 kHz, from about 2 kHz to about 15 kHz, from about 3 kHz to about 12 kHz, from about 3.5 kHz to about 10 kHz, from about 4 kHz to about 8 kHz, from about 4 kHz to about 6 kHz, or about 5 kHz. The current may be applied in single pulse or in a series of repeated pulses. The pulses may be of any duration suitable for the intended diagnostic or therapeutic effect. For example, the length of the pulses may be about 0.01 ms, about 0.02 ms, about 0.05 ms, about 0.1 ms, about 0.2 ms, about 0.5 ms, about 1 ms, about 2 ms, about 5 ms, about 10 ms, about 20 ms, or about 50 ms.

An advantage of the methods of the invention is that they can deliver magnetic fields of high intensities into interior regions of a body part. For example, the interior region of the body part may be at least 1 cm, at least 2 cm, at least 3 cm, at least 4 cm, at least 5 cm, at least 6 cm, at least 7 cm, at least 8 cm, at least 9 cm, or at least 10 cm from one or both surfaces of the body part that are proximal to the flux concentrators. At a specified depth, the magnetic field strength may be from about 0.5 T to about 4 T, from about 1 T to about 3 T, from about 1.5 T to about 2.5 T, at least 0.5 T, at least 1 T, at least 1.5 T, at least 2 T, at least 2.5 T, or at least 3 T.

The method may be used for the treatment of a disease or condition. The disease or condition may affect the brain. For example, the disease or condition may be addiction, Alzheimer's disease, anxiety disorder, chronic pain, depression, essential tremor, hippocampal sclerosis, memory disorders, mesial temporal sclerosis (MTS), neurodegenerative conditions, obesity, obsessive compulsive disorders, Parkinson's disease, seizure, substance abuse, stroke, temporal lobe epilepsy (TLE), tinnitus, or tremors.

The invention also encompasses methods that involve rotating a device of the invention around a body part and applying current to the coil from a plurality of locations to direct magnetic fields to an interior region of the body part. In such methods, the current is applied to the coil at a sufficiently rapid frequency to prevent re-polarization of the interior region as the device is rotated, such that the magnetic stimulation of the interior region is higher than at other regions interposed between the interior region and the flux concentrators.

EXAMPLES

Example 1

Numerical Analysis.

At this stage, the proposed setup has been simulated and systematically analyzed by the Ansoft Maxwell software package (ANSYS Inc.).

Model.

Preliminary simulations were performed using a concentric spheres model of the head. The model consisted in three concentric spherical shells and one sphere in the center, representing the scalp, the skull, the CSF, and the brain, respectively. The electromagnetic properties of the various parts of the brain were acquired from literature [6], [7]. The spheres were truncated at the distance of 30 mm from the center of the spheres at angle 45 degree in order to get a better fit to the anatomy of the brain. However, the spherical model is a good first approximation of the head anatomy for proof of concept purposes and is commonly used for standardized evaluation of TMS coils penetration and focusing.

Coils.

The coils' current were designed to generate magnetic field strength of 2 T in the desired deep region (4 cm depth) when the setup is being used. Coils had 12 turns winding and carried 10 kA sinusoidal current, operating at frequency of 5 kHz, because the TMS excitation is supposed to operate at frequency range of 3.5-10 kHz for most medical applications.

Example 2

Figure 3:
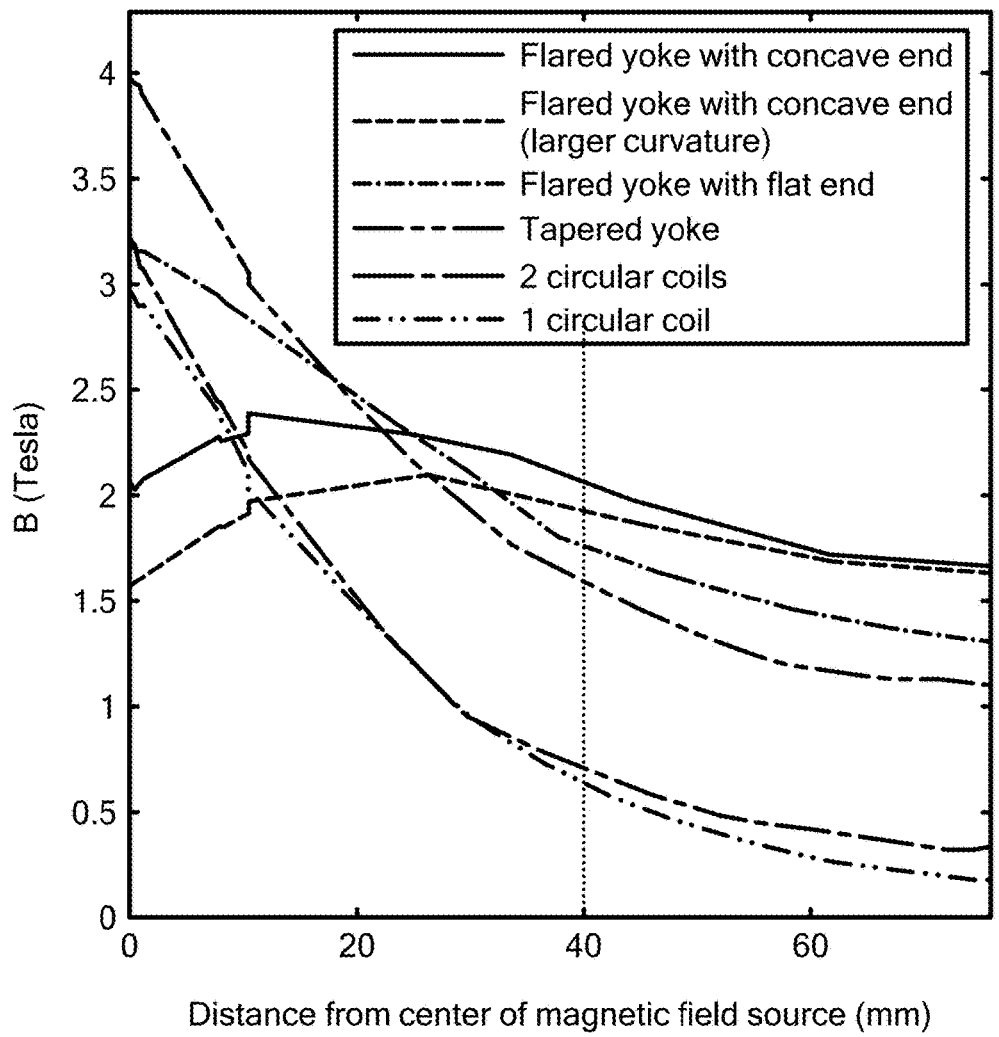
FIG. 3 is a graph of magnetic field intensity vs. distance from the center of magnetic field source along the line from the center of the magnetic field source to the center of the model of a head. The following magnetic field sources were used: a single circular coil configured without a yoke (1 circular coil), a pair of diametrically opposed circular coils configured without a yoke (2 circular coils), a yoke having a pair of diametrically opposed tapered termini with flat endcaps (tapered yoke), a yoke having a pair of diametrically opposed flared termini with flat endcaps (flared yoke with flat end), a yoke having a pair of diametrically opposed flared termini with concave endcaps having radii of curvature of 8 cm and surface diameters of 8.5 cm (flared yoke with concave ends), and a yoke having a pair of diametrically opposed flared termini with concave endcaps having radii of curvature of 4 cm and surface diameters of 8.5 cm (flared yoke with concave ends [larger curvature]).

The depth of magnetic fields produced by different excitation designs was tested by measuring the magnetic field as a function of distance from the point on the scalp of the model head, right under the center of the coil or center of the yoke's end, along the radial direction to the center of the model brain. FIG. 3 demonstrates the penetration pattern of 6 different stimulation experiments.

In the first experiment, one coil was positioned at distance 8 mm above the scalp. As can be seen in FIG. 3, the induced magnetic field at 2 cm depth was nearly 2 T lower than the magnetic field on the scalp. In the second experiment, two coils with opposite polarity were positioned on the opposite sides of the head. The penetration pattern did not appreciably change with respect to case 1 due to the great distance that separates the excitation coils.

In the next four experiments, an iron yoke was used to reconfigure the stimulation field pattern. Four different yoke end shapes, selected for these experiments are: a yoke having a pair of diametrically opposed tapered termini with flat endcaps ("tapered yoke"), a yoke having a pair of diametrically opposed flared termini with flat endcaps ("flared yoke with flat end"), a yoke having a pair of diametrically opposed flared termini with concave endcaps having radii of curvature of 8 cm and surface diameters of 8.5 cm ("flared yoke with concave ends"), and a yoke having a pair of diametrically opposed flared termini with concave endcaps having radii of curvature of 4 cm and surface diameters of 8.5 cm ("flared yoke with concave ends [larger curvature]"). As shown in FIG. 3, comparison between penetration patterns of these four stimulation setups reveals the increased field penetration into the deep regions of the brain.

Figure 4:
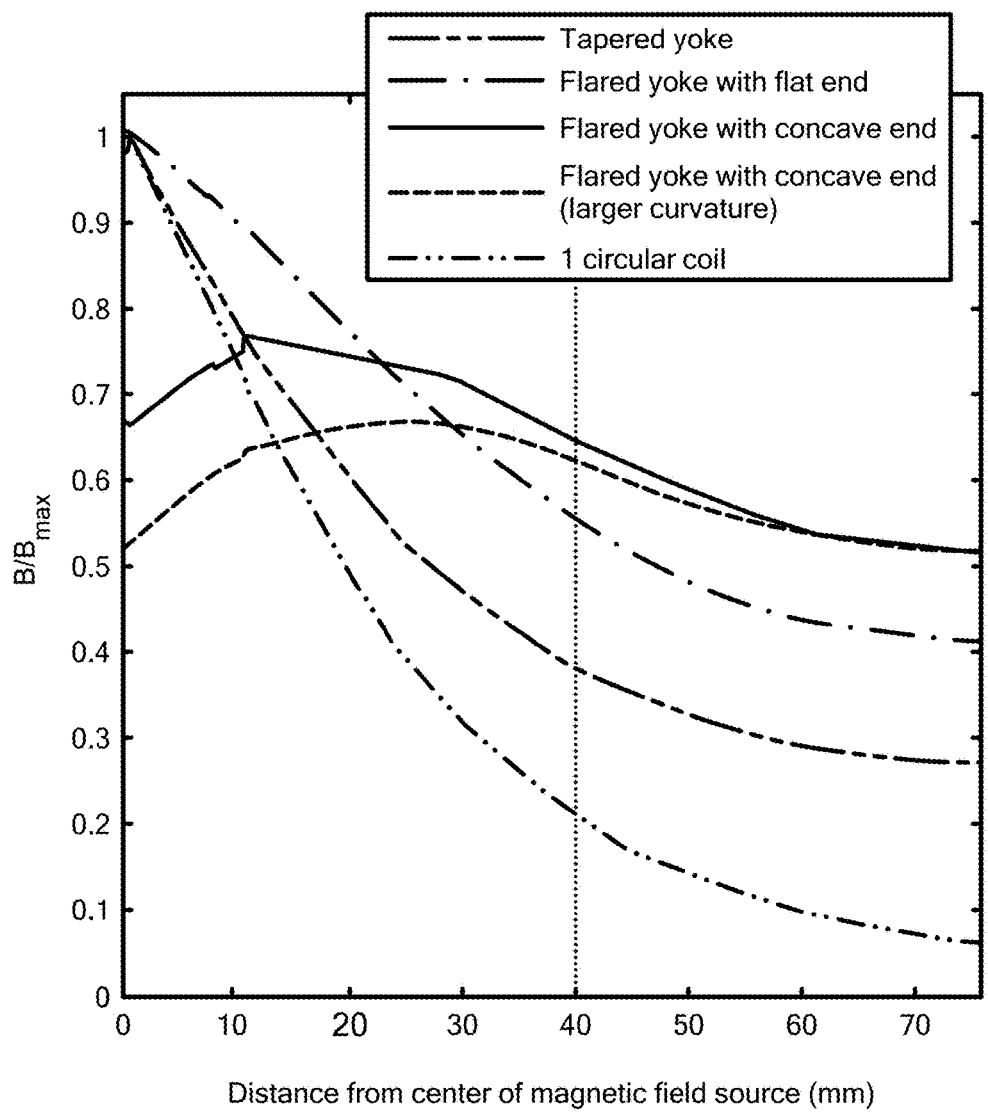
FIG. 4 is a graph of relative magnetic field intensity vs. distance from the center of magnetic field source along the line from the center of the magnetic field source to the center of the model of a head. The following magnetic field sources were used: a single circular coil configured without a yoke (1 circular coil), a pair of diametrically opposed circular coils configured without a yoke (2 circular coils), a yoke having a pair of diametrically opposed tapered termini with flat endcaps (tapered yoke), a yoke having a pair of diametrically opposed flared termini with flat endcaps (flared yoke with flat end), a yoke having a pair of diametrically opposed flared termini with concave endcaps having radii of curvature of 8 cm and surface diameters of 8.5 cm (flared yoke with concave ends), and a yoke having a pair of diametrically opposed flared termini with concave endcaps having radii of curvature of 4 cm and surface diameters of 8.5 cm (flared yoke with concave ends [larger curvature]). $B_{max}$ is defined as the peak magnetic field on any point of the surface of the model head.

The normalized magnetic field to the maximum field on the scalp of discussed designs is demonstrated in FIG. 4. The magnetic field is maintained almost constant throughout the brain, from the scalp down to the center of the concentric sphere and shells, by using a yoke with a flared terminus and concave endcap. A field of 2 T can be observed at depths between 4.0 cm and 7.0 cm.

Example 3

Figures 5A, 5B:
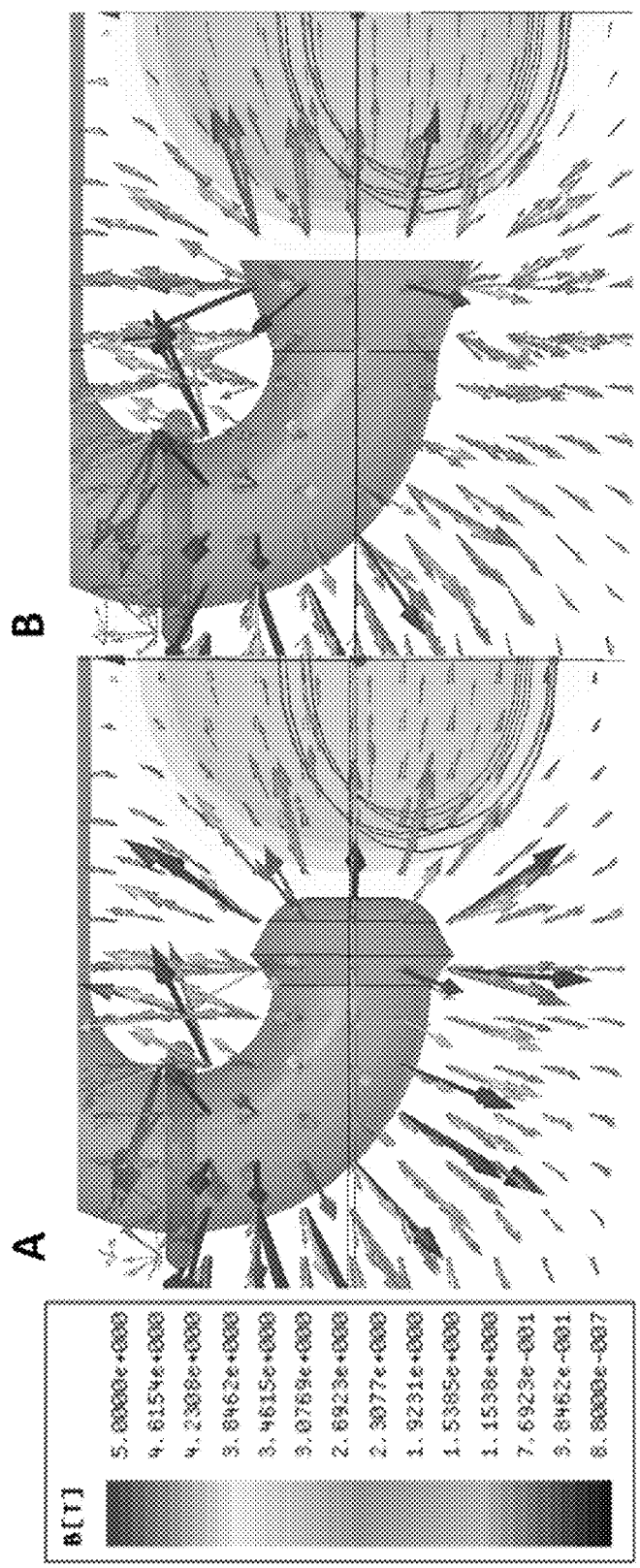
FIG. 5A is a schematic of the magnetic field vector pattern from one end of a yoke having a pair of diametrically opposed tapered termini with flat endcaps, as used in FIGS. 3 and 4. Arrows represent the direction and magnitude of the magnetic field emitted from the surface of the yoke.
FIG. 5B is a schematic of the magnetic field vector pattern from one end of a yoke having a pair of diametrically opposed flared termini with flat endcaps, as used in FIGS. 3 and 4. Arrows represent the direction and magnitude of the magnetic field emitted from the surface of the yoke.
Figures 5C, 5D:
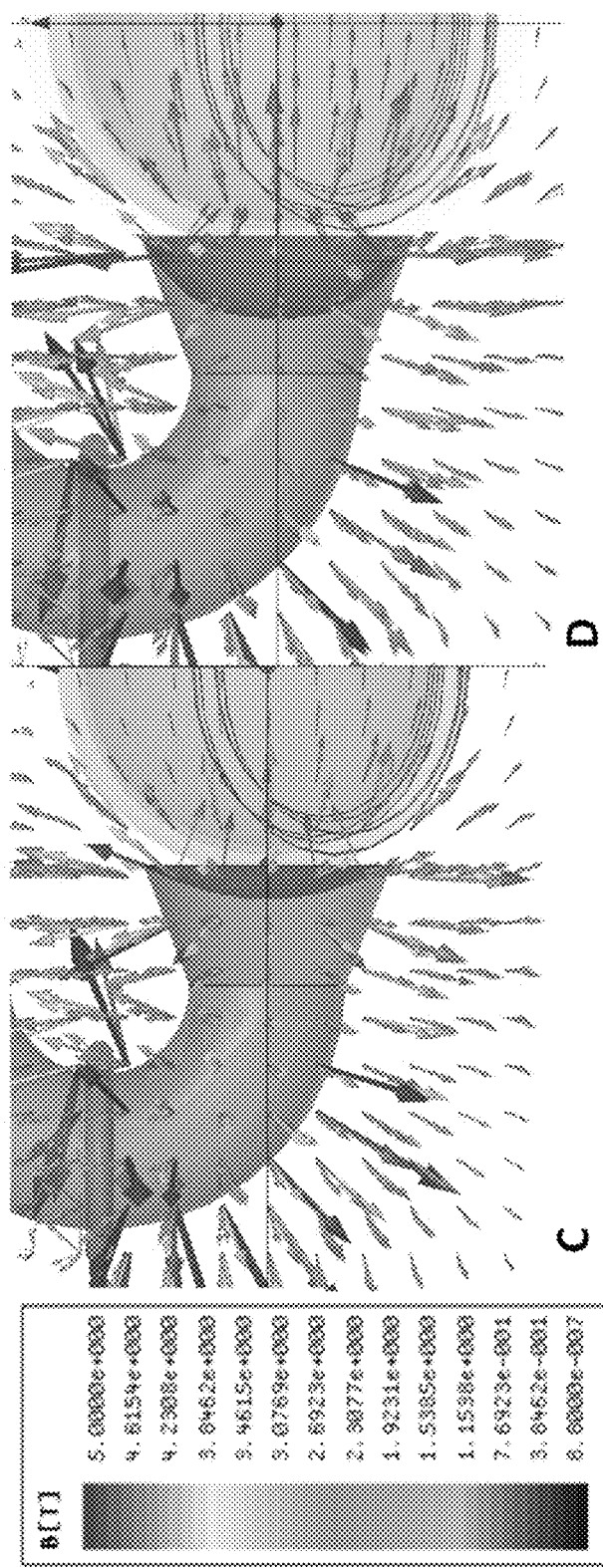
FIG. 5C is a schematic of the magnetic field vector pattern from one end of a yoke having a pair of diametrically opposed flared termini with concave endcaps having radii of curvature of 8 cm and surface diameters of 8.5 cm, as used in FIGS. 3 and 4. Arrows represent the direction and magnitude of the magnetic field emitted from the surface of the yoke.
FIG. 5D is a schematic of the magnetic field vector pattern from one end of a yoke having a pair of diametrically opposed flared termini with concave endcaps having radii of curvature of 4 cm and surface diameters of 8.5 cm, as used in FIGS. 3 and 4. Arrows represent the direction and magnitude of the magnetic field emitted from the surface of the yoke.

FIG. 5 demonstrates the magnetic field vector pattern of four different yoke designs. The arrows indicate the direction of the magnetic field. Comparison of FIGS. 5A-5D confirms the reconfiguration of the flux flow, toward the convergence along the radial direction to the center of the model brain. As a result, the magnetic field vector alignment along the radial direction is much stronger than magnetic field vectors pointing along non-radial directions in the yoke having a deeply concave endcap, as shown in FIG. 5D. In comparison, the yokes with flat endcaps have magnetic vector patterns that have almost the same strength in all directions, as shown in FIGS. 5A and 5B.

Example 4

Figure 6A:
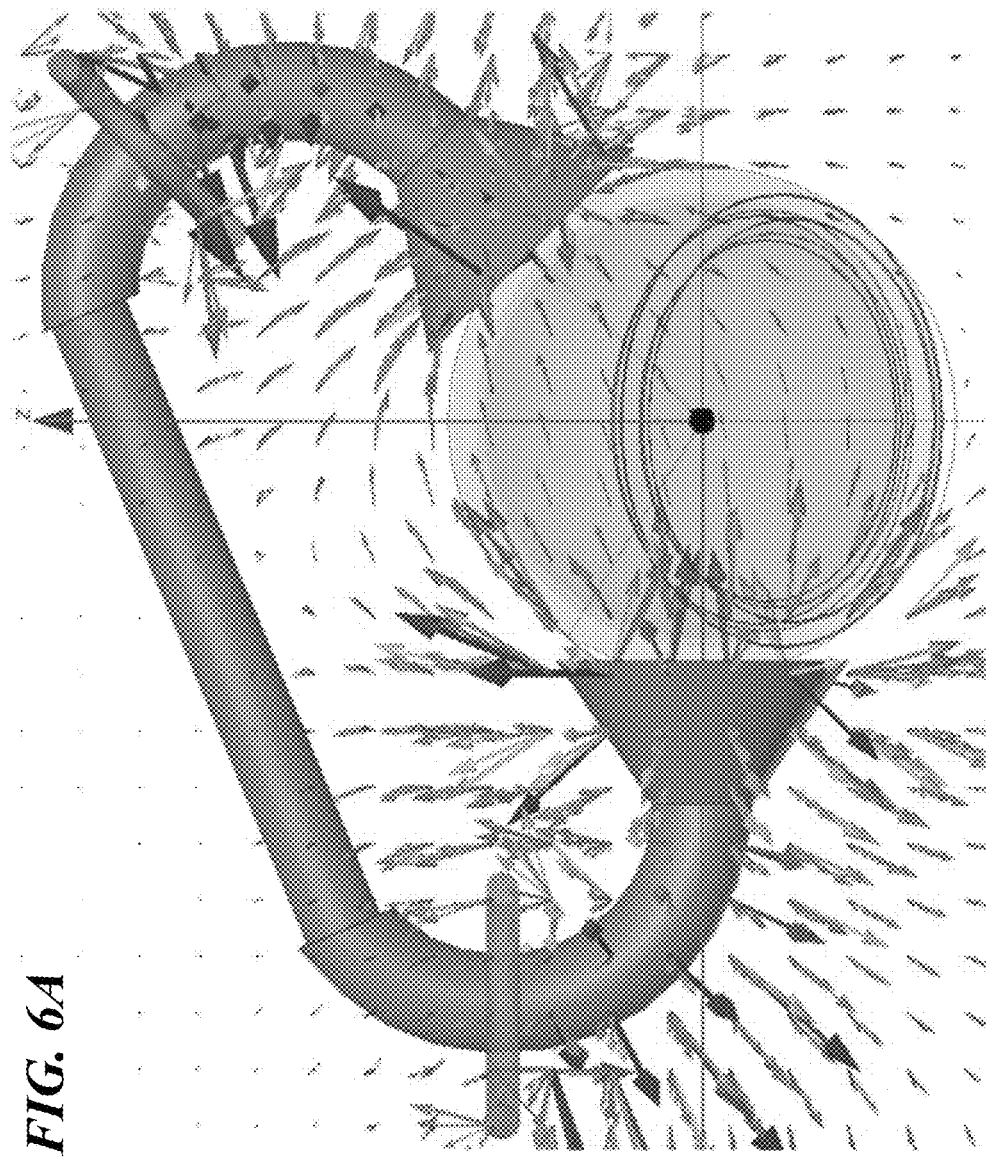
FIG. 6A is a schematic of the magnetic field vector pattern from a yoke having endcaps positioned at a 135° angle. Arrows represent the direction and magnitude of the magnetic field emitted from the surface of the yoke.
Figure 6B:
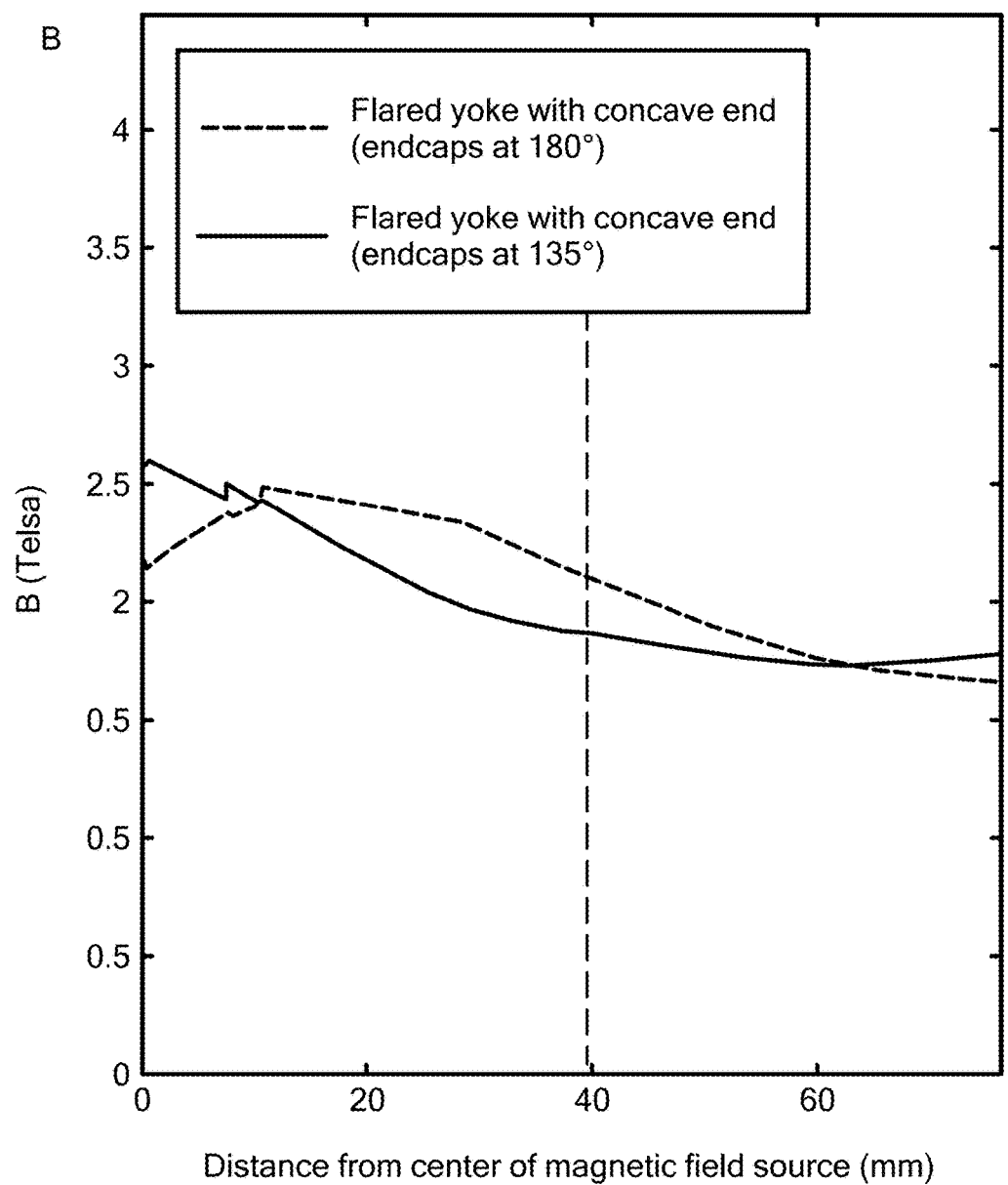
FIG. 6B is a graph magnetic field intensity vs. distance from the center of endcap along the line from the center of the endcap to the center of the model of a head. The following magnetic field-generating devices were used: yoke having flared concave ends positioned at a 180° angle (dashed line), and yoke having flared concave ends positioned at a 135° angle (solid line).

In order to target different regions of the brain, the endcaps' location and angle has to be engineered accordingly. The maximum penetration depth and therefore the highest efficiency will be achieved when the yoke ends are positioned at a 180° angle. However, yoke arrangements in which the yoke ends are positioned at other angles may be used. The magnetic field vector distribution of yoke having ends positioned at a 135° angle are shown in FIG. 6A. As shown in FIG. 6B, a yoke having ends positioned at a 135° angle is still capable of delivering a magnetic field of nearly 2 T at a depth of 4 cm.

REFERENCES

1. Rossi, S., M. Hallett, P. Rossini, A. Pascual-Leone, "Safety, ethical considerations, and applications guidelines for the use of Transcranial magnetic stimulation in clinical practice and research, Clinical Neurophysiology, 120, 2008-2039, 2009.
2. Salvador R., P. C. Miranda, Y. Roth, and A. Zangen, "High-Permeability Core Coils for Transcranial Magnetic Stimulation of Deep Brain regions", Proceedings of IEEE EBMS, August, 2007.
3. Xu, G., Y. Chen, S. Yang, M, Wang, W. Yan, "The Optimal Design of Magnetic Coil in Transcranial Magnetic Stimulation", Proceedings of IEEE, Engineering in Medicine and Biology, September 2005.
4. Lu, M. and S. Ueno, "Calculating the Induced Electromagnetic Fields in Real Human Head by Deep Transcranial magnetic Stimulation", Proceedings of IEEE EBMS, July 2013.
5. Gomez, L, F. Cajko, L. Hernandez-Garcia, A. Grbic, E. Michielssen, "Numerical Analysis and Design of Single-Source Multicoil TMS for Deep and Focused Brain Stimulation", IEEE Transactions on Biomedical Engineering, Vol. 60, No. 10, October 2013.
6. S. Gabriel, R. W. Lau, C. Gabriel, "The Dielectric Properties of Biological Tissues: III Parametric Models for the Dielectric Spectrum of Tissues," Physics in Medicine and Biology, Vol. 41, Issue 11, pp. 2271-2293, 1996.
7. C. Gabriel and S. Gabriel. (YEAR) Compilation of the dielectric properties of body tissues at RF and microwave frequencies. Armstrong Lab., Online: Online: http://www.brooks.af.mil/AFRL/HED/hedr/eports/dielectric/home.html
8. Exposure to high frequency electromagnetic fields, biological effects and health consequences (100 KHz-300 GHz), ICNIRP (International Commission on Non-Ionizing Radiation Protection) 16/2009.

What is claimed is:

1. A device for directing a magnetic field into a body part of a subject, the device comprising:
   (a) a ferromagnetic yoke having a first end and a second end, the first and second ends disposed on opposite ends of the yoke, the yoke comprising:
      (i) a first flux concentrator terminating the first end of the yoke;
      (ii) a second flux concentrator terminating the second end of the yoke; and
      (iii) a connecting element connecting the first and second flux concentrators; and
   (b) at least one coil surrounding the connecting element of the yoke, the coil capable of carrying an electric current that generates a magnetic field along the yoke, wherein the first and second flux concentrators are separated by a gap sufficient to accommodate said body part, wherein the yoke is flared in regions comprising the first and the second flux concentrators, and wherein each of the first and second flux concentrators comprises a concave spherical cap.

2. The device of claim 1, wherein the first end has an essentially circular cross-section in a plane orthogonal to a longitudinal axis of the yoke at the first end, and the second end has an essentially circular cross-section in a plane orthogonal to a longitudinal axis of the yoke at the second end.

3. The device of claim 1, wherein a longitudinal axis of the yoke at the first end and a longitudinal axis of the yoke at the second end intersect at an angle of from about 90° to about 270°.

4. The device of claim 3, wherein the angle is about 180°.

5. The device of claim 1, wherein adjacent to the flared regions the yoke is tapered in regions comprising the first and second flux concentrators.

6. The device of claim 1, wherein the device is capable of providing a magnetic field having an intensity of
   (a) not more than 4 T at the first end and second end of the yoke; and (b) at least 1 T at a distance of 4 cm along a longitudinal axis of the yoke extending from the first end and along a longitudinal axis of the yoke extending from the second end.

7. The device of claim 1, wherein the ferromagnetic yoke comprises a material selected from the group consisting of a silicon steel, a metallic glass, and a ferrite.

8. The device of claim 1, wherein the first and second ends have maximal diameters of from about 1 cm to 100 cm.

9. The device of claim 1, wherein said at least one coil comprises a first coil at a first distance along a longitudinal length of the connecting element from the first end and a second coil at a second distance along the connecting element from the second end, the first and second distances being about equal.

10. The device of claim 1, wherein a distance across the gap between a center of the first end and a center of the second end is from about 10 cm to about 40 cm.

11. The device of claim 1, wherein the concave spherical caps of the first and second flux concentrators have radii of curvature from about 1 cm to about 100 cm.

12. The device of claim 1, wherein said body part is selected from the group consisting of a head, neck, skull, brain, chest, abdomen, limb, arm, hand, leg, and foot.

13. The device of claim 1, further comprising a coil not surrounding the yoke that is capable of modifying the magnetic field within said body part.

14. A system comprising:
(a) the device of claim 1;
(b) a controller; and
(c) a power supply capable of providing an alternating current to the at least one coil, thereby generating a magnetic field between the first and second flux concentrators.

15. The system of claim 14, further comprising a coil not surrounding the yoke that is capable of modifying the magnetic field within said body part.

16. A method of directing a magnetic field into a body part of a subject, the method comprising the steps of:
(a) positioning the device of claim 1 so that said body part is within said gap, said body part having a first surface adjacent to a first end of the yoke and a second surface adjacent to the second end of the yoke; and
(b) applying an alternating electric current to the at least one coil, whereby a magnetic field is generated in an interior region of said body part.

17. The method of claim 16, wherein the interior region is at least 4 cm from the first and second surfaces of said body part.

18. The method of claim 16, wherein the magnetic field has an intensity of:
(a) not more than 4 T at the first and second surfaces of said body part; and
(b) at least 1 T at said interior region at a distance of 4 cm from the first surface of said body part along a longitudinal dimension extending from the first end of the yoke and from the second surface of said body part along a longitudinal dimension extending from the second end of the yoke.

19. The method of claim 18, wherein the magnetic field has an intensity of not more than 3 T at the first and second surfaces of said body part.

20. The method of claim 18, wherein the magnetic field has an intensity of at least 1.5 T at said interior region at a distance of 4 cm from the first surface of said body part along a longitudinal dimension extending from the first end of the yoke and from the second surface of said body part along a longitudinal dimension extending from the second end of the yoke.

21. The method of claim 20, wherein the at least one coil comprises a coil positioned at least 2 cm from each of the first and the second surfaces of said body part.

22. The method of claim 16, wherein the current has an amplitude of from about 6 kA to about 15 kA.

23. The method of claim 16, wherein the alternating current has a frequency of from about 3.5 kHz to about 10 kHz.

24. The method of claim 16, wherein said body part is selected from the group consisting of a head, neck, skull, brain, chest, abdomen, limb, arm, hand, leg, and foot.

25. The method of claim 16, wherein the interior region of said body part is selected from the group consisting of the anterior cingulate gyms, anterior cingulate, anterior limb of the internal capsule, dorsal cingulate gyms, globus pallidus extema, hippocampus, nucleus accumbens, posterior cingulate gyms, septal nucleus, subgenual cingulate gyms, subthalamic nucleus, ventrolateral nucleus of thalamus, and ventromedial nucleus of thalamus.

26. The method of claim 16, wherein the method is for the treatment of a disease or medical condition.

27. The method of claim 26, wherein the disease or condition is selected from the group consisting of addiction, Alzheimer's disease, anxiety disorder, chronic pain, depression, essential tremor, hippocampal sclerosis, memory disorders, learning disabilities, mesial temporal sclerosis (MTS), neurodegenerative conditions, obesity, obsessive compulsive disorders, Parkinson's disease, seizure, substance abuse, stroke, epilepsy, temporal lobe epilepsy (TLE), tinnitus, and tremors.

* * * * *

UNITED STATES PATENT AND TRADEMARK OFFICE
CERTIFICATE OF CORRECTION

PATENT NO. : 9,925,388 B2  
APPLICATION NO. : 14/670214  
DATED : March 27, 2018  
INVENTOR(S) : Parisa Andalib, Francesca Scire Scappuzzo and Vincent Harris Page 1 of 1

It is certified that error appears in the above-identified patent and that said Letters Patent is hereby corrected as shown below:

On the Title Page  
Item [57], ABSTRACT:  
Line 2, replace "party" with --part--.

Signed and Sealed this  
Thirtieth Day of October, 2018

Andrei Iancu  
*Director of the United States Patent and Trademark Office*